(12) United States Patent
Chen et al.

(10) Patent No.: US 9,624,162 B2
(45) Date of Patent: Apr. 18, 2017

(54) METHOD FOR PREPARING 3-AMINOMETHYL-3,5,5-TRIMETHYL CYCLOHEXYLAMINE

(71) Applicants: Wanhua Chemical Group Co., Ltd., Yantai (CN); Wanhua Chemical (Ningbo) Co., Ltd., Ningbo (CN)

(72) Inventors: Changsheng Chen, Yantai (CN); Jinke Jiang, Yantai (CN); Zhongying Chen, Yantai (CN); Jiaoying Cui, Yantai (CN); Jing Wang, Yantai (CN); Fuguo Li, Yantai (CN); Chengge Lv, Yantai (CN); Wenjuan Zhao, Yantai (CN); Yuan Li, Yantai (CN); Weiqi Hua, Yantai (CN)

(73) Assignee: Wanhua Chemical Group Co., Ltd. (CN)

( * ) Notice: Subject to any disclaimer, the term of this patent is extended or adjusted under 35 U.S.C. 154(b) by 18 days.

(21) Appl. No.: 14/648,533

(22) PCT Filed: Dec. 7, 2012

(86) PCT No.: PCT/CN2012/086169
§ 371 (c)(1),
(2) Date: May 29, 2015

(87) PCT Pub. No.: WO2014/086039
PCT Pub. Date: Jun. 12, 2014

(65) Prior Publication Data
US 2015/0315133 A1    Nov. 5, 2015

(51) Int. Cl.
*C07C 253/30*    (2006.01)
*C07C 209/52*    (2006.01)
*C07C 209/48*    (2006.01)

(52) U.S. Cl.
CPC .......... *C07C 253/30* (2013.01); *C07C 209/48* (2013.01); *C07C 209/52* (2013.01); *C07C 2101/14* (2013.01)

(58) Field of Classification Search
None
See application file for complete search history.

(56) References Cited

U.S. PATENT DOCUMENTS

| 3,356,913 A | 12/1967 | Earley |
| 5,166,444 A | 11/1992 | Hutchmacher et al. |

(Continued)

FOREIGN PATENT DOCUMENTS

| CN | 1047855 A | 12/1990 |
| CN | 1047856 A | 12/1990 |

(Continued)

OTHER PUBLICATIONS

Extended European Search Report for Application No. 12889458.1 dated Dec. 8, 2015.

(Continued)

*Primary Examiner* — Sudhakar Katakam
*Assistant Examiner* — Jennifer C Sawyer
(74) *Attorney, Agent, or Firm* — Lerner, David, Littenberg, Krumholz & Mentlik, LLP

(57) ABSTRACT

The present invention provides a method for preparing 3-aminomethyl-3,5,5-trimethyl cyclohexylamine. The method comprises: a) reacting 3-cyano-3,5,5-trimethyl cyclohexanone with excess primary amine as well as removing the water generated from the reaction, so that IPN is substantially converted into imine compounds; b) in the presence of an ammonolysis catalyst, mixing the product of step a) with liquid ammonia, making the imine compound perform ammonolysis reaction to generate 3-cyano-3,5,5-trimethyl cyclohexylimine and the primary amine; and c) in (Continued)

the presence of hydrogen and a hydrogenation catalyst, hydrogenating 3-cyano-3,5,5-trimethyl cyclohexylimine obtained in step b) to obtain 3-aminomethyl-3,5,5-trimethyl cyclohexylamine. The method of the present invention avoids the generation of 3,5,5-trimethyl cyclohexanol and 3-aminomethyl-3,5,5-trimethyl cyclohexanol as the major by-products in the prior art, thereby improving the yield of 3-aminomethyl-3,5,5-trimethyl cyclohexylamine.

25 Claims, 1 Drawing Sheet

(56) References Cited

U.S. PATENT DOCUMENTS

| | | |
|---|---|---|
| 5,679,860 A | 10/1997 | Haas et al. |
| 5,705,699 A | 1/1998 | Witzel et al. |
| 6,022,999 A | 2/2000 | Voit et al. |
| 2002/0173676 A1 | 11/2002 | Ostgard et al. |
| 2010/0036168 A1 | 2/2010 | Ernst et al. |
| 2010/0048954 A1 | 2/2010 | Vedage et al. |
| 2011/0313188 A1 | 12/2011 | Wigbers et al. |

FOREIGN PATENT DOCUMENTS

| | | |
|---|---|---|
| CN | 1483016 A | 3/2004 |
| CN | 101568516 A | 10/2009 |
| CN | 101747205 A | 6/2010 |
| CN | 102307659 A | 1/2012 |
| DE | 3011656 A1 | 10/1981 |
| EP | 0394967 A1 | 10/1990 |
| EP | 0394968 A1 | 10/1990 |
| JP | 03047156 | 2/1991 |
| JP | 03068541 A | 3/1991 |
| JP | 04264057 A | 9/1992 |
| JP | 08253444 | 1/1996 |
| JP | 09059226 A | 3/1997 |
| JP | 2005532725 A | 10/2005 |

OTHER PUBLICATIONS

Russian Office Action for Application No. 2015118247.04(028334) dated Jul. 5, 2016.
Japanese Office Action for Application No. 2015-545627 dated May 24, 2016.
International Search Report for Application No. PCT/CN2012/086169 dated Aug. 8, 2013.

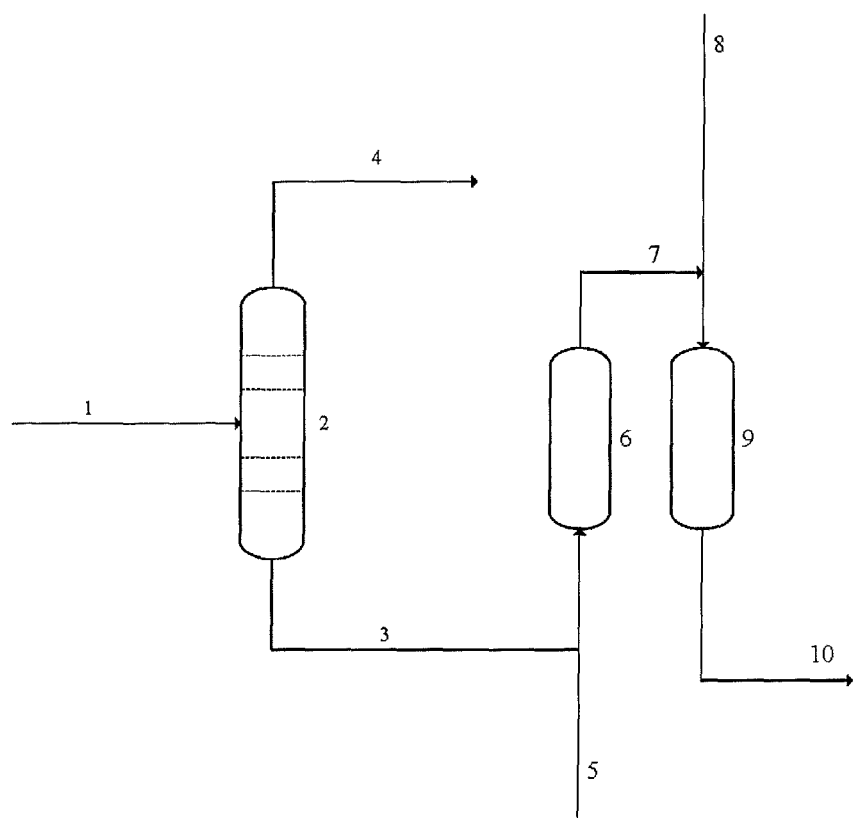

METHOD FOR PREPARING 3-AMINOMETHYL-3,5,5-TRIMETHYL CYCLOHEXYLAMINE

CROSS-REFERENCE TO RELATED APPLICATION

The present application is a national phase entry under 35 U.S.C. §371 of International Application No. PCT/CN2012/086169, filed Dec. 7, 2012, published in Chinese, incorporated herein by reference.

FIELD OF THE INVENTION

The present invention relates to a method for preparing an aliphatic amine, and particularly relates to a method for preparing 3-aminomethyl-3,5,5-trimethyl cyclohexylamine from 3-cyano-3,5,5-trimethyl cyclohexanone.

BACKGROUND OF THE INVENTION

3-Aminomethyl-3,5,5-trimethyl cyclohexylamine (also known as isophorone diamine (IPDA)) is a raw material for preparing 3-isocyanatomethylene-3,5,5-trimethylcyclohexyl isocyanate (also known as isophorone di-isocyanate (IPDI)), polyamide and the like, it can also be used as a curing agent for epoxy resin.

On an industrial scale, IPDA is achieved as follows: reacting 3-cyano-3,5,5-trimethyl cyclohexanone (also known as isophorone nitrile, IPN) with ammonia to form 3-cyano-3,5,5-trimethyl cyclohexylimine (also known as isophorone imine, IPNI), and conducting a reductive amination reaction between IPNI and hydrogen in the presence of ammonia in a catalytic manner. The reaction process thereof is as following:

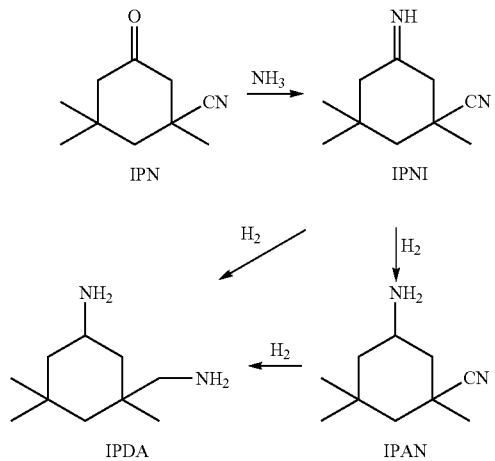

U.S. Pat. No. 3,352,913 discloses a method for preparing IPDA in which IPN reacts with ammonia and hydrogen under the action of Group VIII metal supported catalysts. In this method, the mole ratio of ammonia to IPN (hereinafter referred to as cyanamide ratio) is from 10 to 30, the reaction temperature is from 70° C. to 130° C., and hydrogen pressure is 150 atm. Because the reaction of IPN with ammonia resulting in IPNI is a reversible reaction and IPN cannot be totally converted into IPNI, a part of the unreacted IPN is also hydrogenated and formed 3-amino-3,5,5-trimethyl-cyclohexanol (IPAA) which is hardly separated from IPDA. The yield of this method is only 80%.

CN101568516A discloses a method for preparing IPDA, after the imidization of IPN, the feed stream containing IPNI is reacted with hydrogen and ammonia in the presence of a hydrogenation catalyst. This method is characterized in that, after a portion of IPNI has been reacted, the reaction mixture is contacted with a basic compound other than ammonia and/or a basic catalyst to increase the alkalinity of the reaction mixture during the reaction. This method controls the occurrence of direct hydrogenation of unreacted IPN by adjusting the IPNI feed stream to be alkalinity during the reaction. However, the further addition of base will exacerbate the detaching of cyano group in IPN, generating CN⁻ and 3,5,5-trimethyl-2-cyclohexenone. CN⁻ may affect the activity of hydrogenation catalyst and shorten its life. The hydrogenation of 3,5,5-trimethyl-2-cyclohexenone will produce a by-product of 3,5,5-trimethyl-cyclohexanol with an undesired yield of IPDA.

At present, there are defects in all industrial methods for preparing IPDA:

1) As the reaction of IPN with excess ammonia generating IPNI is a reversible reaction, IPN cannot be completely converted into IPNI, which results in a portion of IPN entering into the hydrogenation reaction system and being directly hydrogenated into IPAA.

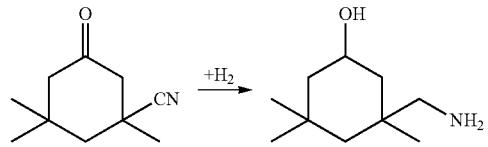

2) Under the basic conditions, the cyano group of IPN is extremely unstable and very easy to be detached and forms 3,5,5-trimethyl-2-cyclohexenone, while 3,5,5-trimethyl-2-cyclohexanol, which is the product of hydrogenation of 3,5,5-trimethyl-2-cyclohexenone, is an undesired product. Moreover, because the process of decyanation reaction may produce free CN⁻, this may lead to a decrease in the activity of hydrogenation catalyst.

In the conventional preparation methods, the reaction of IPN with excess ammonia generates IPNI and water, while the generated water binds to the remaining ammonia which makes the reaction system show alkalinity, thus the decyanation reaction of IPN is unavoidable.

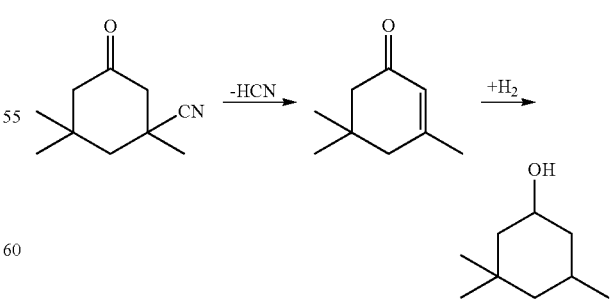

Although the method disclosed in CN101568516A lowers the yield ratio of IPAA by increasing the alkalinity of IPNI reaction liquid, the addition of extra base exacerbates the decyanation reaction of IPN.

DETAILED DESCRIPTION OF THE INVENTION

The objective of the present invention is to provide a novel method for preparing 3-aminomethyl-3,5,5-trimethyl cyclohexylamine (IPDA). Said method can effectively avoid the generation of the above two by-products, namely 3,5,5-trimethyl-cyclohexanol and IPAA, and then improves the yield of IPDA.

The method for preparing 3-aminomethyl-3,5,5-trimethyl cyclohexylamine (IPDA) of the present invention comprises the following steps:

a) reacting IPN with excess primary amine as well as removing generated water, so that IPN is substantially converted into imine compounds; b) in the presence of an ammonolysis catalyst, mixing the product of step a) with liquid ammonia, making the imine compounds perform ammonolysis reaction to generate IPNI and the primary amine; and c) in the presence of hydrogen and the hydrogenation catalyst, hydrogenating the obtained IPNI in step b) to obtain IPDA.

The reaction route of the present invention is shown as following:

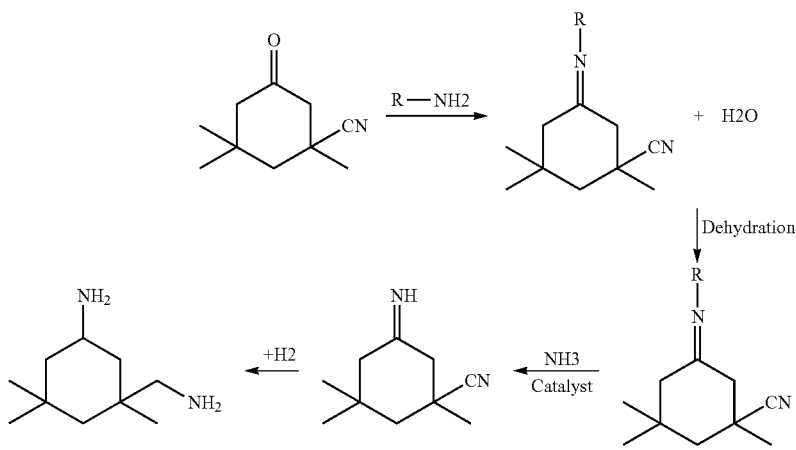

According to an embodiment of the present invention, the primary amine in step a) can be any type of primary amines, for example, it can be a fatty amine or an aromatic amine else. According to an embodiment, as long as the hydrocarbonyl primary amine can be separated from IPDA and does not render side reaction with the reactants or products, it can be used in the present invention. It can be selected from, for instance, alkyl amines, cycloalkyl amines, aryl amines, arylalkyl amines, and the like. The primary amine can be a mono-amine or a multi-amine else, such as a diamine. Specifically, a primary amine can be selected from $C_{1-30}$ alkyl amines, $C_{3-30}$ cycloalkyl amines, $C_{6-30}$ aryl amines, and $C_{7-30}$ arylalkyl amines; preferably selected from $C_{1-10}$ alkyl amines, $C_{3-10}$ cycloalkyl amines, $C_{6-10}$ aryl amines, and $C_{7-10}$ arylalkyl amines. More specifically, a primary amine can be, but not limited to, methylamine, ethylamine, propylamine, butylamine, ethylenediamine, propylenediamine, butanediamine, pentanediamine, hexamethylenediamine, cyclopropane amine, cyclopentane amine, cyclohexane amine, aniline and benzyl amine. The most preferred primary amines are those being easily separated from IPDA and having low boiling points, such as, but not limited to, methylamine, ethylamine, propylamine, butylamine, ethylenediamine, propylenediamine, butanediamine, hexamethylenediamine, aniline, and the like. According to a more preferred embodiment of the present invention, the primary amines having their boiling points between 110° C. and 235° C. are preferred. In another embodiment of the present invention, which is also the most preferred embodiment, IPDA which does not require a separation is used, that is, the target product itself acts as a primary amine.

According to an embodiment of the present invention, the imidization reaction of IPN with the primary amine in step a) is carried out between 20° C. and 150° C., preferably between 40° C. and 120° C., more preferably between 50° C. and 80° C.

According to an embodiment of the present invention, the imidization reaction of IPN with the primary amine in step a) can be performed under the atmospheric pressure or a reduced pressure. Preferably, the reaction is performed under a reduced pressure. The reaction pressure can be 100 kPa or less, preferably 50 kPa or less, more preferably 20 kPa or less.

According to an embodiment of the present invention, the primary amine in step a) is excess, so that IPN reacts as completely as possible. Specifically, the mole ratio of the total amino groups (—$NH_2$) in the primary amine to IPN is in the range of 1-20, preferably in the range of 1-10, more preferably in the range of 2-8. The excess primary amine is advantageous for the reaction, but the cost of the primary amine's recovery increases if the ratio of the primary amine is too high.

According to an embodiment of the present invention, the method used in step a) for separating water from the reaction mixture can be any known suitable method, such as adsorption, extraction, distillation, or the like. Preferably, distillation, particularly the method of distillation under a reduced pressure, is used to dehydrate. The person skilled in the art should understand that, when the method of reduced pressure distillation is used, primary amines having their boiling points higher than that of water (100° C. under a standard atmospheric pressure) should be chosen, and those having their boiling points equal to 110° C. or higher are preferred. According to a preferred embodiment, the boiling point of a primary amine is 235° C. or less, so that it is easy to be separated from IPDA.

According to a preferred embodiment of the present invention, the water content of the product obtained in step a) should be as low as possible, thereby facilitating the equilibrium of the imidization reaction to continuously move towards the direction of the imine products. But considering the efficiency and cost of the reaction, the water content of the resulting product should be 300 ppm or less, preferably 200 ppm or less, more preferably 100 ppm or less.

According to a preferred embodiment of the present invention, the reaction and the separation apparatus used in step a) can be any suitable conventional apparatus, which can be selected and assembled in accordance with the practical requirements. For example, they can be selected from, but not limited to, a reactor and a fixed bed with water-absorbing agents, or a reactor and a fixed bed with a distillation/rectification device. A reactor apparatus with a distillation/rectification device is preferred. These apparatuses are well-known to the person skilled in the art, so it will not go into further details herein.

According to an embodiment of the present invention, the ammonolysis catalyst used in step b) can be an acid metal oxide selected from, for example, but not limited to, γ-alumina, titania, zirconia, silica, zeolite, and the like. γ-Alumina is preferred.

It is more advantageous to use more liquid ammonia in step b). According to an embodiment of the present invention, the mole ratio of said liquid ammonia to IPN used as a raw material in step a) is 5-200, preferably 10-100, more preferably 15-30.

According to an embodiment of the present invention, step b) is carried out at the temperature of 20-200° C. and under the pressure of 10-30 MPa, preferably at the temperature of 50-150° C. and under the pressure of 10-20 MPa, more preferably at the temperature of 80-120° C. and under the pressure of 10-15 MPa.

According to the method of the present invention, step b) can be carried out in a tank reactor or in a fixed bed reactor else, preferably in a fixed bed reactor. These reactors are well-known to the person skilled in the art, so it will not go into further details herein.

According to an embodiment of the present invention, the hydrogenation catalyst in step c) can be any conventional hydrogenation catalyst, for example, a supported catalyst, such as $Co/Al_2O_3$, a Raney metal catalyst, such as Raney cobalt or Raney nickel. Raney nickel and Raney cobalt are preferred. Raney nickel is more preferred.

According to an embodiment of the present invention, the reaction conditions of step c) can be conventional conditions of performing the reductive amination reaction. Specifically, it can be performed at the temperature of 100-200° C. and under the pressure of 10-30 MPa, preferably at the temperature of 100-150° C. and under the pressure of 10-20 MPa, more preferably at the temperature of 120-150° C. and under the pressure of 10-15 MPa.

According to an embodiment of the present invention, step c) can be carried out in any conventional rector, for example, a tank reactor, a fixed bed reactor, a fluidized bed reactor. It is preferably to perform in a tank reactor and a fixed bed reactor, more preferably in a fixed bed reactor. It will not go into further details herein.

According to a preferred embodiment of the present invention, when a fixed bed is used as a reactor, the mole ratio of hydrogen to IPNI is 10-100, preferably 20-80, more preferably 30-50.

When the primary amine used in step a) is IPDA, at least a portion of the final resulting IPDA is returned to step a) and acts as the primary amine to perform imidization reaction with IPN.

When the primary amine used in step a) is not IPDA, the method according to the present invention further comprises step d): separating the primary amine from IPDA in the product obtained in step c) by rectification, wherein the primary amine is returned to step a) for recycling use.

In the method of the present invention, wherein IPN is used as the raw material to prepare IPDA, the primary amine is used to perform the imidization reaction, thereby facilitating the equilibrium of the imidization reaction to continuously move towards the direction of the imine products simply by dehydrating, so that IPN is substantially converted into an imine compound. On the one hand, the method according to the present invention avoids the cyano group of unreacted IPN being detached under the basic conditions and thereby forming 3,5,5-trimethyl-2-cyclohexenone which is further hydrogenated to 3,3,5-trimethylcyclohexanol, and avoids unreacted IPN being directly hydrogenated to IPAA, thus the yield is increased significantly. On the other hand, the method also avoids the trouble of separating the alcohol-type by-products from IPDA. Further, the primary amine can be easily separated from IPDA after the reaction and can be substantially recovered and recycled. Particularly, as to the best embodiment in which IPDA is used as the primary amine, the operation is easier.

DESCRIPTION OF DRAWINGS

FIG. 1 is a schematic of the reaction system used in the method, according to an embodiment of the present invention.

DETAILED EMBODIMENTS

The present invention is further described by, but not limited to, examples with reference to the drawing.

The present invention provides a novel method for preparing IPDA from IPN. In comparison with the method in the prior art in which ammonia and IPN are reacted to form IPNI, the method of the present invention uses the primary amine and IPN to react and form corresponding imine compounds. Since the primary amine is used, water generated in the reaction can be easily removed from the reaction mixture, thereby facilitating the equilibrium of the imidization reaction to continuously move towards the direction of the imine products, and finally, IPN is substantially converted into the imine compound. Afterwards, the resulting imine products are converted into IPNI by using liquid amines, and IPDA is achieved by reductive amination.

The method of the present invention is further described as follows with reference to FIG. 1

FIG. 1 is a schematic of the reaction system used in the method, according to an embodiment of the present invention. Firstly, in step (a), IPN and excess ammonia (1) enter reactive rectification column (2) and react, while water and the reaction mixture are separated in the rectification column. Water (4) is withdrawn from the top of the column, and dehydrated product (3) is drained out from the bottom of the column.

Dehydrated product (3) mainly contains said imine compounds, unreacted primary imines and trace of water. In order to react IPN completely, the water content in dehydrated product (3) should be as low as possible, for example, 300 ppm or less, preferably 200 ppm or less, more preferably 100 ppm or less.

Then, in step (b), dehydrated product (3) and liquid ammonia (5) together enter into an ammonolysis reactor (6) with the ammonolysis catalyst to prepare IPNI. The reactor can be a tank reactor, but preferably a fixed bed reactor. The mixture (7) containing IPNI and the primary amine which is used as the raw material in step (a) is obtained via reactions.

Finally, in step (c), the mixture (7) obtained in step (b) and hydrogen (8) together enter into the hydrogenation reactor (9) and undergo a hydrogenation reaction with obtaining IPDA mother liquid (10). In this step, the reaction conditions identical to conventional hydrogenation reaction of IPNI are used. Hydrogenation catalyst is preferably selected from Raney nickel or Raney cobalt, and Raney nickel is more preferably. Preferably, a fixed bed reactor is used as the reactor, meanwhile, the mole ratio of hydrogen to IPNI is 10-100, preferably 20-80, more preferably 30-50.

The obtained IPDA mother liquid (10) can be treated with any conventional separation/purification to obtain IPDA. When the primary amine used is other than IPDA, IPDA and the primary amine can be separated by the rectification apparatus and the like (not shown in FIG. 1).

The present invention is further illustrated by examples below, and the person skilled in the art should know that the present invention is not limited to these examples.

In the following examples, the quantitative analysis of IPNI (7) and IPDN mother liquid (10) is performed on Aglient-7980 Gas Chromatography. The gas chromatography analysis conditions are as follows:
Chromatographic Column: Aglient IIP-5 (Size: 30 m×0.32 mm×0.25 mm)
Inlet temperature: 280° C.
Split ratio: 30:1
Column flow: 1.5 ml/min
Column temperature: initial: 100° C.
    Heating rate: 15° C./min, increasing to 260° C. and maintaining at 260° C. for 8 minutes
Detector temperature: 280° C.
$H_2$ flow: 35 ml/min
Air flow: 350 ml/min

EXAMPLE 1

This example is carried out using the reactor apparatus as shown in FIG. 1.

Reactive rectification column (2) has an inner diameter of 40 mm, a length of 1000 mm, θ ring packing of 2 mm is installed inside, and a feeding port is located in the middle of the reactive rectification column. Reactor (6) has a length of 200 mm, an inner diameter of 25 mm, and γ-alumina beads with 1 mm in diameter mounted in the reactor. Reactor (9) has a length of 400 mm, an inner diameter of 25 mm, and G62RS hydrogenation catalyst (from Süd-Chemie, Germany) with 1 mm in diameter mounted in the reactor.

Step 1, from the middle of reactive rectification column (2), IPN of 165 g/h and IPDA of 510 g/h enter into the reactive rectification column which is controlled at 50 kPa via a vacuum pump, wherein the reactor temperature is about 200° C., and the temperature of the top of the column is about 81° C.

Step 2, the product from the bottom of the rectification column and liquid ammonia enter into reactor (6) via a high pressure pump for ammonolysis reaction, wherein the feeding rate of liquid ammonia is 425 g/h, the reaction temperature is controlled at 100° C., and pressure is controlled at 15 MPa.

Step 3, the product of ammonolysis is mixed with hydrogen and then entered into reactor (9) for a hydrogenation reaction, wherein the temperature of reactor (6) is controlled at 100° C., and in the reactor (9) the temperature is controlled at 140° C., the pressure is controlled at 15 MPa, and the hydrogen feeding rate is 100 NL/h.

The analysis of sample (3) taken from the bottom of the reactive rectification column (2) shows that the water content thereof is about 150 ppm;

The analysis of sample (10) taken from the outlet of hydrogenation reactor (9) shows that the composition of product is in Table 1 below.

TABLE 1

| Composition of Product | Content (wt %) |
|---|---|
| IPDA | 99.7 |
| bi-IPDA | 0.15 |
| Others | 0.15 |

IPAA and 3,3,5-trimethyl-cyclohexanol are not detected, which belong to the main by-products in the conventional methods.

After the deduction of IPDA in the starting materials, the yield of the reaction is about 98.8%.

In which, the structure of bi-IPDA is shown as follows:

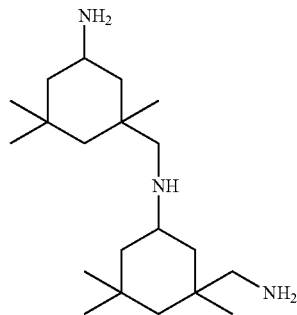 [SMILES: CC1(C)CC(N)CC(C)(CNC2CC(C)(C)CC(C)(CN)C2)C1]

EXAMPLES 2-4

Examples 2-4 are carried out according to the method identical to that of Example 1, except that the IPDA which is used as a primary amine in the first step is replaced by ethylene diamine, hexamethylene diamine and aniline, respectively.

The products' composition of hydrogenation reaction has also been analyzed. The results are shown in Table 2 below.

TABLE 2

| Serial Number | | Example 2 | Example 3 | Example 4 |
|---|---|---|---|---|
| Primary amines used | | ethylene diamine | hexamethylene diamine | aniline |
| Composition of product (wt %, after deduction of the primary amine) | IPDA | 98.5 | 98.4 | 98.5 |
| | Others | 1.15 | 1.19 | 0.98 |
| | bi-IPDA | 0.35 | 0.41 | 0.52 |
| Actual yield of IPDA (%) | | 98.5 | 98.4 | 98.5 |

IPAA and 3,3,5-trimethyl-cyclohexanol are not detected, which belong to the main by-products in the conventional methods.

EXAMPLES 5-7

Examples 5-7 are carried out according to the method identical to that of Example 1, except that γ-alumina which is used as an ammonolysis catalyst in the second step is replaced by commercial available 1 mm titania beads, silica beads, and ion exchange resin (Nankai University, D72).

The products' composition of hydrogenation reaction has also been analyzed. The results are shown in Table 3 below.

TABLE 3

| Serial Number | | Example 5 | Example 6 | Example 7 |
|---|---|---|---|---|
| Ammonolysis catalyst | | titania | silica | D72 |
| Composition of product (wt %, including IPDA of the primary amine) | IPDA | 99.59 | 99.53 | 99.62 |
| | Others | 0.2 | 0.28 | 0.23 |
| | bi-IPDA | 0.21 | 0.19 | 0.15 |
| Actual yield of IPDA (%) | | 98.4 | 98.12 | 98.48 |

IPAA and 3,3,5-trimethyl-cyclohexanol are not detected, which belong to the main by-products in the conventional methods.

EXAMPLES 8-10

Examples 8-10 are carried out according to the method identical to that of Example 1, except that Süd-Chemie G62RS (Germany) which is used as a hydrogenation catalyst in the third step is replaced by Raney nickel (cat-1600) supplied by Catalloy company, and Raney cobalt (GRACE-2800) and Süd-Chemie G67RS (Germany), respectively.

The products' composition of hydrogenation reaction has also been analyzed. The results are shown in Table 4 below.

TABLE 4

| Serial Number | | Example 8 | Example 9 | Example 10 |
|---|---|---|---|---|
| Hydrogenation catalyst | | Cat-1600 | Grace-2786 | G-67RS |
| Composition of product (wt %, including IPDA of the primary amine) | IPDA | 99.60 | 99.57 | 99.60 |
| | Others | 0.20 | 0.28 | 0.23 |
| | bi-IPDA | 0.20 | 0.15 | 0.17 |
| Actual yield of IPDA (%) | | 98.40 | 98.28 | 98.40 |

IPAA and 3,3,5-trimethyl-cyclohexanol are not detected, which belong to the main by-products in the conventional methods.

EXAMPLES 11-13

Examples 11-13 are carried out according to the method identical to that of Example 1, except that the reaction pressures in the second and the third steps are adjusted to 10 MPa, 12 MPa, 13 MPa, and all other conditions are the same as those in Example 1.

The products' composition of hydrogenation reaction has also been analyzed. The results are shown in Table 5 below.

TABLE 5

| Serial Number | | Example 11 | Example 12 | Example 13 |
|---|---|---|---|---|
| Ammonolysis and hydrogenation pressure | | 10 | 12 | 13 |
| Composition of product (wt %, including IPDA of the primary amine) | IPDA | 99.46 | 99.54 | 99.56 |
| | Others | 0.30 | 0.27 | 0.24 |
| | bi-IPDA | 0.24 | 0.19 | 0.20 |
| Actual yield of IPDA (%) | | 97.84 | 98.16 | 98.20 |

IPAA and 3,3,5-trimethyl-cyclohexanol are not detected, which belong to the main by-products in the conventional methods.

EXAMPLES 14-16

Examples 14-16 are carried out according to the method identical to that of Example 1, except that IPDA which is used as a primary amine in the first step is replaced by ethylene diamine with a feeding rate of 90 g/h, 150 g/h and 240 g/h, respectively.

The products' composition of hydrogenation reaction has also been analyzed. The results are shown in Table 6 below.

TABLE 6

| Serial Number | | Example 14 | Example 15 | Example 16 |
|---|---|---|---|---|
| Feeding rate of ethylene diamine | | 90 g/h | 150 g/h | 240 g/h |
| Composition of product (wt %, after deduction of the primary amine) | IPDA | 98.3 | 98.5 | 98.6 |
| | Others | 1.25 | 1.09 | 1.02 |
| | bi-IPDA | 0.45 | 0.41 | 0.38 |
| Actual yield of IPDA (%) | | 98.3 | 98.4 | 98.6 |

IPAA and 3,3,5-trimethyl-cyclohexanol are not detected, which belong to the main by-products in the conventional methods.

EXAMPLES 17-19

Examples 17-19 are carried out according to the method identical to that of Example 1, except that IPDA which is used as a primary amine in the first step is replaced by ethylene diamine with the feeding rate of liquid ammonia of 255 g/h, 340 g/h and 510 g/h, respectively.

The products' composition of hydrogenation reaction has also been analyzed. The results are shown in Table 7 below.

TABLE 7

| Serial Number | | Example 17 | Example 18 | Example 19 |
|---|---|---|---|---|
| Feeding rate of liquid ammonia | | 255 g/h | 340 g/h | 510 g/h |
| composition of product (wt %, after deduction of the primary amine) | IPDA | 98.4 | 98.3 | 98.5 |
| | Others | 1.15 | 1.29 | 1.12 |
| | bi-IPDA | 0.45 | 0.41 | 0.38 |
| Actual yield of IPDA (%) | | 98.4 | 98.3 | 98.5 |

IPAA and 3,3,5-trimethyl-cyclohexanol are not detected, which belong to the main by-products in the conventional methods.

It can be seen from the above examples that the product yield can be increased significantly and can substantially reach 98% by using the method of the present invention to prepare IPDA. Moreover, this method avoids the generation of by-products IPAA and 3,3,5-trimethyl-cyclohexanol, which eliminates the trouble of separating these alcohol-type by-products and IPDA which are quite difficult to be separated during the purification of products.

Although the present invention is described by specific embodiments as described above, the person skilled in the art should appreciate that any modification, addition or replacement can be done with these embodiments without departure from the spirit of the present invention, and the protection scope of the present invention is defined by the claims but not limited to the specific embodiments listed herein.

The invention claimed is:

1. A method for preparing 3-aminomethyl-3,5,5-trimethyl cyclohexylamine (IPDA), comprising the following steps:
   a) reacting 3-cyano-3,5,5-trimethyl cyclohexanone (IPN) with excess primary amine as well as removing generated water, so that IPN is converted into imine compounds;
   b) in the presence of an ammonolysis catalyst, mixing the product of step a) with liquid ammonia, making the imine compounds perform ammonolysis reaction to generate 3-cyano-3,5,5-trimethyl cyclohexylimine (IPNI) and the primary amine, wherein step b) is carried out at a temperature ranging from 20 to 200° C. and under a pressure ranging from 10 to 30 MPa; and
   c) in the presence of hydrogen and the hydrogenation catalyst, hydrogenating IPNI obtained in step b) to obtain IPDA.

2. The method according to claim 1, characterized in that the primary amine in step a) is a mono-amine or a diamine selected from the group consisting of $C_{1-30}$ alkyl amines, $C_{3-30}$ cycloalkyl amines, $C_{6-30}$ aryl amines, and $C_{7-30}$ arylalkyl amines.

3. The method according to claim 2, characterized in that the primary amine is a primary amine having a boiling point between 110° C. and 235° C.

4. The method according to claim 1, characterized in that the primary amine in step a) is IPDA.

5. The method according to claim 1, characterized in that the mole ratio of the total amino groups (—$NH_2$) of the primary amine to IPN in step a) is in the range of 1-20.

6. The method according to claim 1, characterized in that water is removed by using methods of adsorption, extraction or distillation in step a).

7. The method according to claim 6, characterized in that the distillation method is a method of distillation under a reduced pressure.

8. The method according to claim 7, characterized in that step a) is carried out under the pressure of 100 kPa or less.

9. The method according to claim 1, characterized in that step a) is carried out at 20-150° C.

10. The method according to claim 1, characterized in that the water content of the product obtained in step a) is 300 ppm or less.

11. The method according to claim 1, characterized in that the mole ratio of the liquid ammonia to IPN used as a raw material in step a) is 5-200.

12. The method according to claim 1, characterized in that a fixed bed reactor is used in step c), wherein the mole ratio of hydrogen to isophorone imine is 10-100.

13. The method according to claim 4, characterized in that at least a portion of IPDA obtained in step c) is returned to step a) and acts as the primary amine to perform imidization reaction with IPN.

14. The method according to claim 1, characterized in that the primary amine is not IPDA, and the method further comprises step d): separating the primary amine from IPDA in the product obtained in step c) by rectification, wherein the primary amine is returned to step a) for recycling use.

15. The method according to claim 1, characterized in that step b) is carried out at a temperature of 50-150° C. and under a pressure of 10-20 MPa.

16. The method according to claim 1, characterized in that the ammonolysis catalyst used in step b) is an acid metal oxide selected from the group consisting of γ-alumina, titania, zirconia, silica, and zeolite.

17. The method according to claim 1, characterized in that step c) is carried out at a temperature of 100-200° C. and under a pressure of 10-30 MPa.

18. The method according to claim 1, characterized in that the hydrogenation catalyst used in step c) is selected from Raney metal catalyst.

19. The method according to claim 2, characterized in that the primary amine in step a) is selected from the group consisting of methylamine, ethylamine, propylamine, butylamine, ethylenediamine, propylenediamine, butanediamine, hexamethylenediamine, and aniline.

20. The method according to claim 5, characterized in that the mole ratio of the total amino groups (—$NH_2$) of the primary amine to IPN in step a) is in the range of 1-10.

21. The method according to claim 10, characterized in that the water content of the product obtained in step a) is 200 ppm or less.

22. The method according to claim 10, characterized in that the water content of the product obtained in step a) is 100 ppm or less.

23. The method according to claim 11, characterized in that the mole ratio of the liquid ammonia to IPN used as a raw material in step a) is 10-100.

24. The method according to claim 15, characterized in that step b) is carried out at the temperature of 80-120° C. and under the pressure of 10-15 MPa.

25. The method according to claim 18, characterized in that the hydrogenation catalyst used in step c) is selected from Raney cobalt or Raney nickel.

* * * * *